United States Patent
Lee et al.

(10) Patent No.: US 9,556,341 B2
(45) Date of Patent: *Jan. 31, 2017

(54) POROUS STRUCTURE FOR FORMING ANTI-FINGERPRINT COATING, METHOD OF FORMING ANTI-FINGERPRINT COATING, SUBSTRATE COMPRISING THE ANTI-FINGER-PRINT COATING FORMED BY THE METHOD, AND PRODUCT COMPRISING THE SUBSTRATE

(75) Inventors: Eun Jeong Lee, Daejeon (KR); Young Jun Hong, Daejeon (KR); Hyeon Choi, Daejeon (KR); Taek Ho Yang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 59 days.

This patent is subject to a terminal disclaimer.

(21) Appl. No.: 13/496,859

(22) PCT Filed: Sep. 17, 2010

(86) PCT No.: PCT/KR2010/006444
§ 371 (c)(1),
(2), (4) Date: May 9, 2012

(87) PCT Pub. No.: WO2011/034388
PCT Pub. Date: Mar. 24, 2011

(65) Prior Publication Data
US 2012/0219782 A1  Aug. 30, 2012

(30) Foreign Application Priority Data

Sep. 18, 2009 (KR) .................. 10-2009-0088587
Mar. 31, 2010 (KR) .................. 10-2010-0029245

(51) Int. Cl.
*C09D 5/16* (2006.01)
*C09D 5/00* (2006.01)
(Continued)

(52) U.S. Cl.
CPC .............. *C09D 5/1637* (2013.01); *B05D 1/18* (2013.01); *C09D 5/00* (2013.01); *C09D 5/006* (2013.01);
(Continued)

(58) Field of Classification Search
CPC ......... C12N 11/00; C12N 11/02; C12N 11/08; C12N 11/14; C12N 9/20; C08L 89/00; C09D 5/1637
See application file for complete search history.

(56) References Cited

U.S. PATENT DOCUMENTS 6,342,386 B1   1/2002 Powers
2004/0247895 A1  12/2004 Dreja et al.
(Continued)

FOREIGN PATENT DOCUMENTS

CN  001522286  8/2004
CN  101258196  9/2008
(Continued)

OTHER PUBLICATIONS

Chen et al.; Candida Antarctica Lipase B Chemically Immobilized on Epoxy-Activated Micro- and Nanobeads: Catalysts for Polyester Synthesis; Biomacromolecules; 2008, 9, pp. 463-471.*
(Continued)

*Primary Examiner* — Michael P Rodriguez
(74) *Attorney, Agent, or Firm* — Dentons US LLP

(57) ABSTRACT

Provided are a porous structure for forming anti-fingerprint coating capable of providing a self-cleaning function to a surface of a substrate, a method of forming anti-fingerprint coating using the same, an anti-fingerprint coated substrate prepared by the same method, and a product including the same. When the porous structure including a lipolytic enzyme is formed on the surface of the substrate, contaminants decomposed by an enzyme are absorbed into a pore,
(Continued)

and thus anti-fingerprint coating may be more effectively performed to remove detectable contamination from a surface of the substrate. As a result, contamination by fingerprints on the surface of a display device, the appearance of an electronic device, or building materials can be effectively reduced.

8 Claims, 2 Drawing Sheets

(51) Int. Cl.
    *C09D 7/12*     (2006.01)
    *C12N 9/20*     (2006.01)
    *B05D 1/18*     (2006.01)
    *C08L 89/00*     (2006.01)

(52) U.S. Cl.
    CPC ............ *C09D 5/1687* (2013.01); *C09D 7/125* (2013.01); *C09D 7/1233* (2013.01); *C12N 9/20* (2013.01); *C08L 89/00* (2013.01); *C12Y 301/01003* (2013.01); *Y10T 428/249954* (2015.04); *Y10T 428/249987* (2015.04)

(56) References Cited

U.S. PATENT DOCUMENTS

| | | | |
|---|---|---|---|
| 2006/0232912 A1* | 10/2006 | Lin et al. | .................. 361/600 |
| 2007/0006774 A1 | 1/2007 | Rogers et al. | |
| 2008/0038241 A1* | 2/2008 | Schasfoort et al. | ......... 424/94.3 |
| 2009/0238811 A1* | 9/2009 | McDaniel et al. | ........... 424/94.2 |
| 2011/0312057 A1* | 12/2011 | Buthe | ..................... C12N 9/20 435/198 |

FOREIGN PATENT DOCUMENTS

| | | | |
|---|---|---|---|
| JP | 60-251883 | A | 12/1985 |
| JP | 63-171678 | B2 | 7/1988 |
| JP | 9-118842 | A | 5/1997 |
| JP | 3280024 | | 2/2002 |
| JP | 2002-095471 | A | 4/2002 |
| JP | 2004-530027 | A | 9/2004 |
| JP | 2004530027 | A | 9/2004 |
| JP | 2008-525598 | A | 7/2008 |
| KR | 10-2001-0108263 | A | 12/2001 |
| KR | 10-2003-0011802 | A | 2/2003 |
| WO | 93/13256 | | 7/1993 |
| WO | 9313256 | A1 | 7/1993 |
| WO | 02/098998 | A1 | 12/2002 |
| WO | 02098998 | A1 | 12/2002 |
| WO | 2006/071772 | A2 | 7/2006 |
| WO | 2008/131715 | A1 | 11/2008 |
| WO | 2009/062518 | A1 | 5/2009 |
| WO | 2009062518 | | 5/2009 |

OTHER PUBLICATIONS

Office Action of Japanese Patent Office in Appl'n No. 2012-529690 dated Sep. 8, 2014.
U.S. Appl. No. 13/946,998, filed Jul. 19, 2013.

* cited by examiner

POROUS STRUCTURE FOR FORMING ANTI-FINGERPRINT COATING, METHOD OF FORMING ANTI-FINGERPRINT COATING, SUBSTRATE COMPRISING THE ANTI-FINGER-PRINT COATING FORMED BY THE METHOD, AND PRODUCT COMPRISING THE SUBSTRATE

This application is a National Stage Entry of International Application No. PCT/KR2010/006444, filed Sep. 17, 2010, and claims the benefit of Korean Application No. 10-2010-0029245, filed Mar. 31, 2010 and Korean Application No. 10-2009-0088587, filed on Sep. 18, 2009, both of which are hereby incorporated by reference in their entirety for all purposes as if fully set forth herein.

TECHNICAL FIELD

The present invention relates to a porous structure for forming anti-fingerprint coating capable of providing a self-cleaning function to a surface of a substrate, a method of forming anti-fingerprint coating using the same, an anti-fingerprint coated substrate prepared by the same method, and a product including the same.

BACKGROUND ART

Contamination caused by fingerprints is one of the most frequent contaminations occurring on various display devices, high-glossy electronic devices or building materials. Such contamination is clearly visible and causes an exterior defect on a product. Recently, as the fingerprint contamination on a surface of a display device has increased with the development of touchscreen interface technology of electronic devices, there is an increasing demand for resolving the problem of the fingerprint contamination on the surface of display devices.

However, until now, no technology actually realizing anti-fingerprint coating has been developed, although anti-contamination coating has just been developed in the sense of easy cleaning.

For example, WO09/72738 discloses a anti-fingerprint coating composition for a stainless steel external case of an electronic appliance, which contains 10.6 parts by weight or less of an additive composed of 27.6 to 36.2 parts by weight of polysilicate, 10.6 parts by weight or less of any one selected from epoxy and vinyl resins, 21.2 to 42.6 parts by weight of colloidal silica, at least one selected from the first group consisting of —OH, —NH$_2$, and —COOH, and at least one selected from the second group consisting of —CnF$_{2n+1}$ and —SiR$_3$.

U.S. Patent No. 2002/0192181 discloses an anti-contamination composition, which includes a cured or crosslinked polymer having no perfluoropolyether moieties, and a fluid fluorinated alkyl- or alkoxy-containing polymer or oligomer.

However, the above-mentioned anti-contamination film uses fluorine-based coating, such that a contaminant transferred to its surface is easily wiped due to low surface energy. Since the anti-contamination film does not have a function of self-cleaning, that is, a function of actively reducing transfer of fingerprints or decomposing fingerprints, the appearance may not be improved without wiping the contaminant off.

A conventional anti-fingerprint film can be applied only to a steel plate used for an external case, and has a limit in application to a product requiring high light transmittance such as a display device.

Meanwhile, a coating solution, a coating layer, and a coating method using the same were also developed in the self-cleaning sense using an enzyme. However, the coating solution, layer and method have been developed to prevent adherence of marine microorganisms to the bottom of a ship, but not to reduce contamination caused by fingerprints on display devices, the appearance of electronic devices, and building materials.

For example, a self-polishing, anti-contamination coating composition is disclosed in U.S. Patent No. 2008-0038241, and a method of preventing contamination of an underwater device by marine microorganisms is disclosed in U.S. Pat. No. 5,998,200.

That is, in the self-cleaning sense using an enzyme, the conventional coating solution, layer or method has a mechanism of previously removing an adsorbent material produced by marine microorganisms to prevent marine microorganisms from adhering to the bottom of a ship or removing a contaminant with the adsorbent material, but this mechanism is not associated with the decomposition of the fingerprint contaminant.

As far as the present inventors know, there is no technology of anti-fingerprint coating in the self-cleaning sense, which can be used to provide an anti-fingerprint property to the surface of a display device.

Technical Problem

The present invention is directed to a method of forming anti-fingerprint coating capable of providing a self-cleaning function to a surface of a substrate, an anti-fingerprint coated substrate prepared according to the same method, and a product including the same.

Technical Solution

The present inventors have made much research on a method of forming anti-fingerprint coating capable of providing a self-cleaning function, not simply forming an anti-contamination coating providing an easy cleaning function. In detail, in consideration that the fingerprint is mostly composed of lipids, the present inventors have assumed that when a lipolytic enzyme is coated on a substrate, transferred fingerprints may be reduced by the reaction of the enzyme. Accordingly, the present inventors have confirmed whether such coating provides an anti-fingerprint property by examining a change in a physical property of the fingerprint transferred to the lipolytic enzyme-coated substrate [see Korean Patent Application No. 10-2009-0088587].

While major components of a fingerprint are sweat and sebum, the fingerprint is also composed of dead skin cells from the skin and contaminants such as dusts from an external environment. Among them, it has been known that the main cause leaving stains on the appearance of a product such as an electronic device is sebum, which is composed of lipids including triglycerides, wax monoesters, fatty acids, squalenes, cholesterols, cholesteryl esters, etc. (P. W. Wertz, Int. J Cosmet. Sci. 2009, 31: 21-25). Among the components of the sebum, the triglycerides and wax monoesters account for nearly 70% of the total content of the sebum. These components have a structure in which several fatty acids are bound by ester bonds. When the ester bonds are broken down, the sebum is mainly decomposed into fatty acids, especially, oleic acids, leading to an increase in homogeneity and conversion into lower molecular weight materials. As a result, it is possible to completely release from a product by decomposing the oleic acids into lower molecular weight materials or modifying the oleic acids to increase volatility.

Though the lipolytic enzyme is coated on the surface of the substrate, various contaminations caused by an external environment can be decomposed and reduced to a certain degree. During research on a method of further improving such an effect of removing a contaminant, the present inventors focused on the fact that when a porous structure including a lipolytic enzyme is formed, a contaminant decomposed by the enzyme is absorbed into a pore, which may be effective in removing visible contamination on a surface of the structure. As a result, as shown in FIG. 1, when a fingerprint contaminant interacts with the lipolytic enzyme, it is converted into low molecular weight materials which can be absorbed by the porous structure and rapidly removed from the surface of the structure. Here, the interaction includes a chemical action such as decomposition of fingerprint components by a lipolytic enzyme, and a physical action such as absorption of fingerprint molecules into a pore. Afterwards, fingerprint contaminants partially decomposed or transferred to a pore without decomposition may be completely decomposed by an enzyme included in the pore to be removed. In this manner, the porous structure widens a contact area between the enzyme and the fingerprint contamination to help the decomposition of fingerprint contaminants, and provides a space on its surface in which the fingerprint contaminants acting with the enzyme will be removed, and thus serves to rapidly remove the fingerprint contamination from the surface of the structure. The porous structure may protect the enzyme to raise stability of the enzyme, and serve as a functional film having, for example, anti-scratching and anti-contaminating properties.

Therefore, the present invention is directed to a porous structure including a lipolytic enzyme for forming an anti-fingerprint coating on a surface of a substrate.

Since the porous structure is formed to improve efficiency of anti-fingerprinting coating, the present invention is not limited to its shape. However, the porous structure may have a porosity of 5 to 60%. When the porosity is 5% or less, it is difficult to obtain a desired effect, and when the porosity is 80% or more, the intensity of the coating layer is decreased. The present invention is not particularly limited to a material for the porous structure, either, but may be limited to the material depending on the use of applying anti-fingerprint coating. For example, if a touchscreen interface is disposed on the entire surface of a display device, to prevent screen contamination by fingerprints, the porous structure may have high optical transmittance. Particularly, the porous structure of the present invention can be formed of a siloxane-based composition disclosed in Korean Patent No. 10-0226979 or a composition for a hard coating agent including a silica particle disclosed in Korean Patent No. 10-0569754. The present invention is not limited to a method of forming a porous structure or a method of introducing a lipolytic enzyme to the porous structure, either, and thus specific examples will be described below.

Meanwhile, the porous structure may have a thickness of 20 nm to 200 μm, but is not limited thereto. However, the thickness of the porous structure should be controlled to a level that does not inhibit an optical characteristic required for the substrate. That is, when the porous structure has a thickness of less than 20 nm, the decomposition of the fingerprint components may be limited, and when the porous structure has a thickness of more than 200 μm, the optical transmittance may be decreased.

In the present invention, the lipolytic enzyme includes any enzymes having a characteristic of hydrolyzing lipid components of a fingerprint such as triglycerides, wax monoesters, fatty acids, squalenes, cholesterols and cholesteryl esters.

An example of an enzyme having an activity to hydrolyze ester bonds at room temperature is a lipase. The present invention is not limited to the kind or origin of the lipase, and thus any type of lipase may be used as the lipolytic enzyme according to one embodiment of the present invention. To obtain a high degree of hydrolysis with respect to the triglycerides and wax monoesters, which are the main components of the sebum, a lipase non-specifically acting at any position may be used. Currently, various lipases produced using microorganisms may be commercially available from Novozymes or Amano Enzyme, and a lipase may be produced using a transformer into which a backbone gene of the lipase is inserted.

In addition to the lipase, the enzymes having a lipolytic activity are well known in the art. For example, a considerable number of proteases are known as lipolytic enzymes having lipolytic activity, and cutinases are also known to have lipolytic activity.

The porous structure including the lipolytic enzyme for forming anti-fingerprint coating may also include at least one enzyme selected from the group consisting of a protease, an amylase, a cellulase and a lactase. For example, to decompose various kinds of proteins smeared by a fingerprint, a protease may be immobilized on the surface of the product. The protease is used to break peptide bonds between proteins and thereby remove contamination. In addition, to remove components of sweat and components derived from various external contaminants, an enzyme such as an amylase, a cellulase or a lactase may be used.

The present invention is also directed to a method of forming anti-fingerprint coating including forming a porous structure including a lipolytic enzyme on the surface of a substrate. The present invention is not particularly limited to the method of forming the porous structure on the substrate.

For example, a porous coating layer may be prepared by a sol-gel method using tetramethoxysilane (TMOS), tetraethoxysilane (TEOS), or glycidoxypropyl trimethoxysilane (GPTMS). A long-chain organic material such as polyethylene glycol diacrylate was coated and cured, and then a crosslinking agent was added thereto to reinforce a mechanical strength, thereby coating a hydrogel having a double network. Therefore, the porous coating layer may be completed. Alternatively, a silica nanoparticle is added to an acrylate-based organic compound to coat, and thus a more porous structure may be formed, compared to when only an organic compound is coated.

An additional treatment may be needed to enlarge a pore size of the porous structure formed as described above. For example, when the porous coating layer is prepared by the sol-gel method, a surfactant may be added to a coating solution to coat and then cured, and the surfactant may be removed by heating or plasma treatment, thereby enlarging the size of the pore. Alternatively, the porous structure having a larger pore size may be formed by removing a silica particle added to an acrylate by etching the porous coating layer, which is formed by mixing an acrylate and a silica particle, with an HF solution or leaving a silica particle layer by removing an acrylate through plasma treatment or annealing.

The present invention is not particularly limited to a sequence of introducing a lipolytic enzyme to the porous structure to prepare the anti-fingerprint film. For example, the lipolytic enzyme may be introduced after the porous structure is formed, or may be simultaneously introduced with the formation of the porous structure. A method of immobilizing the enzyme is well known in the art. For example, a lipolytic enzyme may be introduced to the surface of the substrate by adsorption, covalent bonds or encapsulation.

The adsorption refers to adherence of the lipolytic enzyme to the surface of the substrate or porous structure by physical cohesion. A protein constituting the enzyme has strong adsorption to a surface of a material alone. Thus, the lipolytic enzyme may be immobilized to the surface of the substrate by adsorption with no use of an additional treatment process. The following embodiment shows that the immobilization of the lipolytic enzyme by adsorption provides excellent stability.

To introduce the lipolytic enzyme to the surface of the porous structure, there are various known techniques of forming covalent bonds between the porous structure and the enzyme. The techniques use a cyanogen bromide, an acid azide derivative, a condensing reagent, diazo coupling, alkylation, and carrier crosslinking.

For example, the carrier crosslinking technique is a technique of forming covalent bonds between a functional group present on the porous structure using a bifunctional crosslinker and a functional group present on the lipolytic enzyme. Since the lipolytic enzyme has various functional groups in addition to an amino group and a carboxyl group, if a functional group capable of covalently binding to these functional groups is present on the porous structure, the covalent bonds may be easily formed using the bifunctional crosslinker. Here, the functional group present on the porous structure may be a functional group originally present on the porous structure or a functional group introduced to the porous structure to covalently bind to the enzyme. For example, when the porous structure is formed by curing an organic compound such as an acrylate, the organic compound may be mixed with a material having a functional group not participating in the curing. To the porous structure prepared by a sol-gel reaction, a functional group may be introduced by a method of mixing an organic siloxane material having a functional group not participating in the sol-gel reaction. Alternatively, the functional group may be introduced by a post-treatment process such as primer treatment or self-assembled monolayer (SAM) treatment after the porous structure is introduced (coated) on the surface of the substrate.

As the functional group for forming covalent bonds with the enzyme, an amino group, an amide group, a carboxyl group, an aldehyde group, a hydroxyl group, or a thiol group is used, and the functional group present on or introduced to the porous structure may vary according to the kind of the substrate forming the porous structure.

In one embodiment, the covalent bond may be formed by a process including a) treating a surface of a substrate including the porous structure having at least one functional group selected from the group consisting of amino, amide, carboxyl, aldehyde, hydroxyl and thiol groups with a solution including a bifunctional crosslinker; and b) dipping the substrate in a buffer including the lipolytic enzyme.

As the bifunctional crosslinker used to induce formation of the covalent bonds, a bis-imidoester, bis-succinimidyl derivative, bifunctional aryl halide, bifunctional acrylating agent, dialdehyde, or diketone may be used, but the present invention is not limited thereto. An exemplary embodiment of the present invention shows the covalent bond being induced using dialdehyde, for example, glutaraldehyde.

In another embodiment, the covalent bond may be formed by dipping the substrate including the porous structure having an epoxy group in the buffer including the lipolytic enzyme. Furthermore, as the substrate undergoing the above process is treated with heat or UV to a level at which the heat or UV does not degrade the activity of the enzyme, the enzyme may be more strongly immobilized.

A method of immobilizing the enzyme using the covalent bond as described above will be described in further detail with reference to the following exemplary embodiment.

In addition, the encapsulation refers to a method of immobilizing the enzyme by trapping the lipolytic enzyme in between other materials. In an embodiment, the encapsulation may be performed by coating the surface of the substrate with a gel matrix, microcapsule, hollow fiber or membrane, and introducing the lipolytic enzyme. For example, a membrane formed of cellulose such as cellulose nitrate or cellulose acetate, polycarbonate, nylon, or fluororesin such as polyterafluoroethylene may be used.

The coating of the substrate with a gel matrix, microcapsule, hollow fiber or membrane and the introduction of the lipolytic enzyme may be simultaneously or sequentially performed. In other words, the surface of the substrate is first coated with the gel matrix, microcapsule, hollow fiber or membrane, and the substrate is then dipped in the buffer including the lipolytic enzyme. Otherwise, the lipolytic enzyme may be introduced as soon as the surface of the substrate is coated with the gel matrix, microcapsule, hollow fiber or membrane. For example, for the encapsulation technique using the gel matrix, the gel matrix may be coated and cured, and the enzyme may then be adsorbed, or when a sol solution is prepared in a sol-gel reaction, the enzyme may be added to prepare a mixed solution and the substrate may be coated with the mixed solution and then cured.

Among the methods, the encapsulation using the gel matrix is more desirable to retain and further promote the activity of the enzyme. Any kind of a gel ensuring a mechanical strength and an optical property may be applied. For example, the substrate may be primarily coated with a coating layer prepared by a sol-gel method using TMOS, TEOS or GPTMS or a hydrogel formed in a double network by reinforcing a mechanical strength of polyethylene glycol (PEG), and the enzyme is then encapsulated into the primary coating. Further detailed description will be provided in the following exemplary embodiment.

As the buffer including the lipolytic enzyme used in the above-described methods, a phosphate buffered saline (PBS) buffer, potassium phosphate buffer, or sodium phosphate buffer may be used, but the present invention is not limited thereto. An amount of the lipolytic enzyme included in the buffer is determined in principle as an amount enabling the surface of the substrate to be immobilized to be covered in a monolayer. A generally-used lipolytic enzyme is composed of a small amount of enzyme and additives including an excess of an extender such as dextrin or lactose and a stabilizer. Thus, the amount of the enzyme to be added is determined based only on the content of the protein. In the case of the covalent bond, the amount of the enzyme to be added may be determined by calculating a content of the protein corresponding to the functional group of the surface of the substrate, and in the cases of the adsorption and encapsulation, an amount of the enzyme to be added, which is 3 to 10 times the content of the protein capable of covering the surface of the substrate, may be dissolved in the buffer.

Meanwhile, the present invention is not limited to an anti-fingerprint coated substrate, and thus any type of a substrate is applied. For example, products requiring anti-fingerprint coating may be products that are often contacted with hands in everyday life, including display devices, the appearance of electronic devices, or building materials. These products have a surface formed of plastic or glass, or a surface treated by gloss coating such as UV coating or protective coating. In one embodiment, the substrate may be formed of plastic or glass. For example, the substrate may include at least one polymer selected from the group consisting of polyester, polypropylene, polyethyleneterephthalate (PET), polyethylenenaphthalate, polycarbonate, triacetylcellulose, olefin copolymer, and polymethylmethacrylate, or glass. The substrate may be treated on its surface by various coating methods such as gloss coating, protective coating, paint coating, and hydrogel coating.

The present invention is also directed to a substrate having a porous structure formed by the method described above. As seen from the following exemplary embodiment, the substrate having the porous structure having a lipolytic enzyme formed by the method exhibits an excellent anti-fingerprint characteristic because of decomposition of the fingerprints and a decrease in transfer of fingerprints.

To maximize a spreading effect of the fingerprint components, the substrate having the porous structure may have a surface energy of 20 to 50 mN/m. When the surface energy of the anti-fingerprint coating layer is less than 20 mN/m, the fingerprint components may not be spread, and when the surface energy of the anti-fingerprint coating layer is more than 50 mN/m, the fingerprint may be difficult to easily remove. Here, when a lipase is, for example, coated as the enzyme, the coating layer has a surface energy of 30 to 50 mN/m in which the spreading effect of the fingerprint is maximized. As a result, the transfer of the fingerprints is reduced, and the range of the surface energy may be preferred.

The present invention is also directed to product including a substrate having a porous structure. The product including the substrate having the porous structure according to the present invention may be a product that is often contacted with hands in everyday life, and the present invention is not particularly limited to the kind of the product. For example, the product may include display devices, electronic devices, or building materials. The display device may be one selected from the group consisting of a liquid crystal display device (LCD), an organic light emitting diode (OLED), and a plasma display device panel (PDP). Since currently-supplied portable display devices have a touchscreen-type interface, the anti-fingerprint coating according to the present invention may cause a significant improvement of beauty of the product.

The present invention is not particularly limited to a method of introducing anti-fingerprint coating to the product. In other words, the porous structure may be directly formed on a substrate surface of the product such as the display device, or the film-type substrate having the porous structure may be adhered to the surface of the product.

BRIEF DESCRIPTION OF DRAWINGS

The above and other objects, features and advantages of the present invention will become more apparent to those of ordinary skill in the art by describing in detail exemplary embodiments thereof with reference to the adhered drawings, in which.

DETAILED DESCRIPTION OF EXEMPLARY EMBODIMENTS

Figure 1:
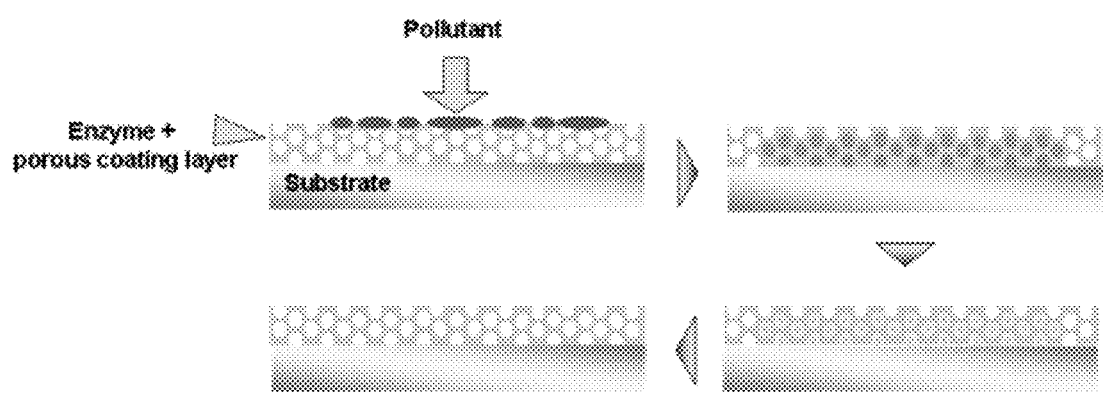
FIG. 1 is a schematic diagram showing a decomposition mechanism of contaminants on an anti-fingerprint coated film of the present invention.

Hereinafter, the present invention will be described with reference to examples and comparative examples in detail. However, the present invention is not limited to these examples.

EXAMPLES

Example 1

Preparation of Anti-Fingerprint Coated Film Using Siloxane-Based Composition and Lipase 250 g of 3-glycidyloxypropyltrimethoxysilane, 100 g of tetraethoxysilane, and 146 g of methanol were stirred in a flask. 7.3 g of aluminum isopropoxide was added to the obtained mixture, and then stirred again until it became a clear solution. The stirred mixture was cooled to 25° C., and 80 g of citric acid aqueous solution having a pH of 2.5 was dropped and then reacted for several hours. In addition, an aqueous solution prepared of excesses of isopropyl alcohol and titanium isopropoxide, and a trace of acetic acid was reacted during reflow, thereby preparing an intermediate derivative of the titanium isopropoxide. After 60 g of the intermediate derivative of the titanium isopropoxide was added and then reacted for approximately 3 hours, 145 g of acetyl acetone was added and then sufficiently stirred. Afterwards, 200 g of colloid silica dispersed in methanol was added and then matured for several hours, thereby preparing a siloxane-based composition.

A slide glass was dipped in the prepared siloxane-based composition to coat, and then cured at 110° C. for 2 hours, and thus a porous structure was prepared on the slide glass.

The slide glass was dipped in a PBS buffer having 100 mg/ml of a lipase (Amano Enzyme; Lipase PS "Amano" SD (23,000 U/g), and then kept at 4° C. for 24 hours. Subsequently, the resulting slide glass was dipped in distilled water to be washed three times for 20 minutes, and blow-dried with nitrogen.

Example 2

Preparation of Anti-Fingerprint Coated Film Using Composition for Hard Coating Agent Including Silica Particles and Lipase A hard coating solution was prepared by uniformly mixing 7 wt % EB1290 (SK UCB Co., Ltd.) as a reactive acrylate oligomer, 29 wt % dipentaerythritol hexacrylate (DPHA) as a multifunctional acrylate monomer, 11 wt % silica dispersed solution (solid content: 30%) having an average particle size of 15 to 20 nm, which was prepared by dispersing silica particles in methyl isobutyl ketone and methanol, 9 wt % dimethyl formamide (DMF) and 12 wt % isopropyl alcohol (IPA) as solvents, 29 wt % of methyl ethyl ketone (MEK), 2 wt % IRG184 as an initiator, and 1 wt % BYK300 as an additive.

The prepared hard coating composition was coated on a PET film and then UV-cured, thereby preparing a porous structure on the PET film.

The slide glass was dipped in a PBS buffer having 100 mg/ml of a lipase (Amano Enzyme; Lipase PS "Amano" SD; 23,000 U/g), and then kept at 4° C. for 24 hours. Subsequently, the resulting slide glass was dipped in distilled water to be washed three times for 20 minutes, and blow-dried with nitrogen.

Example 3

Preparation of Anti-Fingerprint Coated Film Using Siloxane-Based Composition, Lipase, and Protease A slide glass coated with the siloxane-based porous structure prepared as described in Example 1 was dipped in a PBS buffer having 50 mg/ml of a lipase (Amano Enzyme; Lipase PS "Amano" SD; 23,000 U/g) and 50 mg/ml of a protease (Novozymes; Esperase), and kept at 4° C. for 24 hours. Then, the slide glass was dipped in distilled water to be washed three times for 20 minutes, and blow-dried with nitrogen.

Comparative Example 1

Preparation of Lipase-Introduced Anti-Fingerprint Coated Film by Covalent Bonds Using Linkers A glass substrate was coated with a lipase by the following method: A slide glass whose surface was coated with amino alkyl silane was reacted in 10% glutaraldehyde solution for 2 hours. Subsequently, the slide glass was lightly washed with distilled water, dipped in a PBS buffer having 100 mg/ml of a lipase (Amano Enzyme; Lipase PS "Amano" SD; derived from *Burkholderia cepacia*), and then kept at a room temperature for 24 hours. The lipase-immobilized slide glass was sufficiently washed with running distilled water, and washed in distilled water for 40 minutes with gentle shaking. Then, the slide glass was taken out, and blow-dried with compressed nitrogen at room temperature. Thus, the preparation of a lipase-coated glass substrate was completed.

Experimental Example 1

Test for Anti-Fingerprinting Performance

To confirm reduction of contamination on a surface, fingerprints were put on a slide glass prepared by the method described in Example 1, and then the slide glass was put into a temperature and humidity tester under conditions including 50° C. and 30% humidity to measure the change in haze with time. The test was performed four times according to fingerprint transfer.

The results are shown in Table 1 (Change in Haze with Time according to Fingerprint Transfer)

TABLE 1

| Time | Change in Haze Value (ΔH increased by fingerprint transfer) | | | |
|---|---|---|---|---|
| Right After Transfer | 0.8 | 1.4 | 1.9 | 3.2 |
| 1 H | 0.1* | 0.4 | 0.8 | 1.7 |
| 3 H | 0.0* | 0.3* | 0.5 | 1.2 |
| 5 H | 0.0* | 0.2* | 0.2* | 0.7 |
| 24 H | 0.0* | 0.1* | 0.1* | 0.1* |

*level at which it was difficult to detect whether contamination by fingerprints occurred or not at first glance As shown in Table 1, the numbers show that the contaminants were removed with time from the slide glass prepared by Example 1, and thus the haze value was gradually reduced with time.

Figure 2:
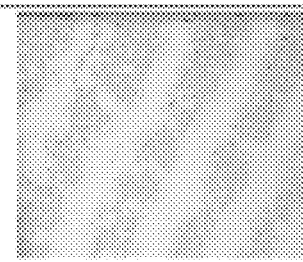
FIG. 2 is a microscopic photograph showing a state in which a surface of a slide glass prepared by a method of examples is contaminated by fingerprints according to time.

Meanwhile, the fingerprint removal with time from the slide glass prepared by Example 1 was examined under a microscope, and then the photograph was compared with that of Comparative Example (reference), that is, the non-anti-fingerprint coated slide glass, in FIG. 2. The microscopic examination was performed with 75× magnification.

As shown in FIG. 2, it was visualized that contaminants were removed from a surface of the slide glass prepared by the method described in Example 1 with time.

Experimental Example 2

Test for Anti-Fingerprinting Performance

To confirm reduction of contamination on a surface, fingerprints were put on a slide glass prepared by the method described in Example 2, and then the slide glass was put into a temperature and humidity tester under conditions including 50° C. and 30% humidity to measure the change in haze with time.

The results are shown in Table 2 (Change in Haze with Time according to Fingerprint Transfer)

TABLE 2

| Time | Change in Haze Value |
|---|---|
| Right After Transfer | 2.4 |
| 2 H | 0.4 |
| 5 H | 0.3 |
| 24 H | 0.3 |

As shown in Table 2, the numbers show that contaminants were removed from a surface of the PET film prepared by the method described in Example 2 with time and the haze values were gradually removed with time.

Experimental Example 3

Test for Anti-Fingerprinting Performance

To confirm reduction of contamination on a surface, fingerprints were put on a slide glass prepared by the methods described in Examples 1 and 3, and then the slide glass was put into a temperature and humidity tester under conditions including 50° C. and 30% humidity to measure the change in haze with time. The results are shown in Table 3 (Change in Haze with Time according to Fingerprint Transfer).

TABLE 3

| Time | Example 1 (Coated with Lipase) Change in Haze Value | Example 3 (Lipase + Protease) Change in Haze Value |
|---|---|---|
| Right After Transfer | 2.1 | 2.0 |
| 2 H | 0.6 | 0.3 |
| 5 H | 0.3 | 0.2 |
| 24 H | 0.1 | 0.0 |

As shown in Table 3, the numbers show that contaminants were removed from a surface of the PET film prepared by the method described in Example 3 with time and the haze values were gradually removed with time. It was confirmed that the performance was improved when the protease was used with the lipase, compared to when the lipase was used alone.

Experimental Example 4

Test for Anti-Fingerprinting Performance

To confirm reduction of contamination on a surface, fingerprints were put on a slide glass prepared by the methods described in Example 1 and Comparative Example 1, and then the slide glass was put into a temperature and humidity tester under conditions including 50° C. and 30% humidity to measure the change in haze with time. The results are shown in Table 4 (Change in Haze with Time according to Fingerprint Transfer).

TABLE 4

| Time | Example 1 (with Porous Coated Layer) Change in Haze Value | Comparative Example 1 (without Porous Coated Layer) Change in Haze Value |
|---|---|---|
| Right After Transfer | 2.1 | 2.4 |
| 2 H | 0.3 | 1.8 |
| 5 H | 0.1 | 1.6 |
| 24 H | 0.0 | 1.2 |

As shown in Table 4, the number shows that contaminants were more easily removed from the slide glass prepared by the method described in Example 1 with time, than from the slide glass prepared by the method described in Comparative Example 1. As a result, it was confirmed that the performance of removing contaminants by the porous structure was significantly improved, compared to when the porous structure was not formed.

When a porous structure including a lipolytic enzyme according to the present invention is formed on a surface of a substrate, contaminants decomposed by an enzyme are absorbed into a pore, and thus anti-fingerprint coating may be more effectively performed to remove detectable contamination from a surface of the substrate. As a result, contamination by fingerprints on the surface of a display device, the appearance of an electronic device, or building materials can be effectively reduced.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A method of forming an anti-fingerprint coating for a display device, comprising:
    providing a substrate of the display device, which is selected from plastic or glass; and
    forming a porous structure on a surface of the substrate to obtain the anti-fingerprint coating,
    wherein the porous structure includes a lipolytic enzyme, and
    wherein the display device is selected from the group consisting of a liquid crystal display device (LCD), an organic light emitting diode (OLED), and a plasma display device panel (PDP).

2. The method according to claim 1, wherein the lipolytic enzyme is a lipase.

3. The method according to claim 2, wherein the porous structure further comprises at least one enzyme selected from the group consisting of a protease, an amylase, a cellulase, and a lactase.

4. The method according to claim 1, wherein the plastic includes at least one polymer selected from the group consisting of polyester, polypropylene, polyethyleneterephthalate, polyethylenenaphthalate, polycarbonate, tri-acetylcellulose, olefin copolymers, and polymethylmethacrylate.

5. The method according to claim 1, wherein the lipolytic enzyme is introduced to the porous structure by an adsorption, covalent bonds or an encapsulation.

6. The method according to claim 5, wherein the covalent bonds are formed through a process including treating the surface of the substrate including the porous structure having at least one functional group selected from the group consisting of amino, amide, carboxyl, aldehyde, hydroxyl and thiol groups with a solution including a bifunctional cross-linker; and dipping the substrate in a buffer including the lipolytic enzyme.

7. The method according to claim 5, wherein the covalent bonds are formed through a process including dipping the substrate including the porous structure having an epoxy group in a buffer including the enzyme.

8. The method according to claim 5, wherein the encapsulation is performed by coating the surface of the substrate with a gel matrix, a microcapsule, a hollow fiber or a membrane, and introducing the lipolytic enzyme.

* * * * *